United States Patent [19]

Bewick

[11] Patent Number: 4,568,641
[45] Date of Patent: Feb. 4, 1986

[54] PROCESS FOR PRODUCING OPTICALLY ACTIVE ARYLOXYPROPIONIC ACIDS AND DERIVATIVES THEREOF

[75] Inventor: David W. Bewick, Bracknell, England

[73] Assignee: Imperial Chemical Industries PLC, London, England

[21] Appl. No.: 634,492

[22] Filed: Jul. 26, 1984

[30] Foreign Application Priority Data

Jul. 27, 1983 [GB] United Kingdom ............... 8320222
Nov. 1, 1983 [GB] United Kingdom ............... 8329086

[51] Int. Cl.$^4$ ..................... C12P 17/12; C07P 41/00
[52] U.S. Cl. ................... 435/122; 435/119; 435/120; 435/121; 435/128; 435/130; 435/135; 435/136; 435/141; 435/146; 435/280
[58] Field of Search ............ 435/280, 119, 120, 121, 435/128, 130, 135, 136, 141, 146, 280

[56] References Cited

U.S. PATENT DOCUMENTS

| | | | |
|---|---|---|---|
| 4,204,044 | 5/1980 | Suhara et al. | 435/280 |
| 4,443,548 | 4/1984 | Oshima et al. | 435/280 |
| 4,461,835 | 7/1984 | Sih | 435/280 |

OTHER PUBLICATIONS

Hutt et al., J. Pharm. Pharmacol., 1983, 35, 693–704.

Primary Examiner—Sam Rosen
Attorney, Agent, or Firm—Cushman, Darby & Cushman

[57] ABSTRACT

A process for the stereospecific inversion of the [S] enantiomer of an α-aryloxypropionic acid of formula I:

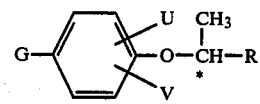

(I)

wherein G is OR$^1$ or

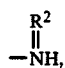

R$^1$ is hydrogen or a protecting group and R$^2$ is hydrogen or methyl, U and V each independently represent hydrogen or halogen, and R is a carboxyl group, or an enzymic equivalent thereof, which process comprises contacting said [S] enantiomer with a microorganism having a stereospecific inverting enzyme system, or with an extract of the microorganism contacting said enzyme system, to convert the [S] enantiomer to the corresponding [R] enantiomer.

11 Claims, No Drawings

PROCESS FOR PRODUCING OPTICALLY ACTIVE ARYLOXYPROPIONIC ACIDS AND DERIVATIVES THEREOF

This invention relates to a stereoselective process for producing individual isomers of optically active compounds, to a micro-organism and to further processing of the isomers.

The compounds to be prepared in the form of one enantiomer by the present process are α-aryloxypropionic acids and their enzymic equivalents (as hereinafter defined).

Previously known commercial methods for producing a single isomer of a compound involved physical, chemical or microbiological techniques. Physical techniques have relied on different physical properties of the isomers in a racemic mixture, eg. different crystallisability (though this is not appropriate to strict enantiomers), chemical techniques have relied on resolution of the chiral centre during production, eg. using a chiral catalyst, while microbiological techniques have generally relied on the use of micro-organisms or their enzymes which are either capable of synthesising the desired isomer or are capable of separating a racemate eg. by chemically modifying one of the isomers such as by degradation of one. In many cases, these techniques have been applied to compounds very early in the route for producing the desired product thereby running the risk that racemisation may occur during one of the subsequent process steps in the route.

It has now been found in accordance with the present invention, that α-aryloxypropionic acids may be stereospecifically "resolved" by means of a microbiological system. In the operation of this system, the [S] enantiomer is inverted to form the [R] enantiomer, while the [R] enantiomer itself remains substantially unaltered. This process thus achieves enrichment of the [R] enantiomer from a racemic mixture rather than separation and wasteful loss of the [S] enantiomer.

Accordingly the present invention provides a process for the stereospecific inversion of the [S] enantiomer of an α-aryloxypropionic acid of the formula:

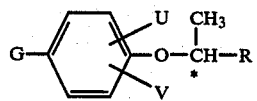

wherein G is OR$^1$ or

R$^1$ is hydrogen or a protecting group and R$^2$ is hydrogen or methyl, U and V each independently represent hydrogen or halogen, and R is a carboxyl group, or an enzymic equivalent thereof, which comprises contacting said [S] enantiomer with a microorganism having a stereospecific inverting enzyme system, or with an extract of the microorganism containing said enzyme system, to convert the [S] enantiomer to the corresponding [R] enantiomer.

Preferably G in formula I is OR$^1$ wherein R$^1$ is as defined above. Examples of R$^1$ as protecting group are alkyl and benzyl.

While it is possible to carry out the process of the invention using an [S] enantiomer in the substantial absence of the [R] enantiomer, the [S] enantiomer will normally be provided as part of the racemate of the particular α-aryloxypropionic acid or equivalent compound. As the enzyme system is stereoselective for the [S] enantiomer and the [R] enantiomer is not significantly altered by it, the resulting mixture is enriched in respect of the [R] enantiomer. Thus, the resulting product formed from the racemate will certainly contain at least 50% of the [R] enantiomer and will normally contain at least 75%, preferably at least 90% up to, in theory, 100% of the [R] enantiomer.

The inversion is performed in the presence of the stereospecific inverting enzyme system which may, if desired, be completely or partially extracted from the micro-organism in which it occurs (ie. in pure or crude form) and may optionally be immobilised. However, it is preferred that the enzyme is present together with at least some of the cellular components of the micro-organism to obviate the need for special separation steps and enzyme purification and/or enzyme immobilisation procedures. The enzyme must be provided in an active and stable form in which the reaction will proceed and, when present in association with the cells, there may in theory be live or dead and be intact, detergent-treated, autolysed or immobilised cells. If desired the detergent-treated autolysed or immobilised cells may be homogenised. Particular methods of immobilising microbial cells include: binding to water-insoluble ion exchangers, via ionic bonds; cross-linking of the cells with a bifunctional reagent eg. glutaraldehyde; entrapping into a natural or synthetic polymer matrix where they are physically restrained, eg. using polyacrylamide, collagen, cellulose triacetate, agar, alginate such as calcium alginate, or polystyrene; binding to membrane reactors; liquid membrane encapsulation; polyelectrolyte flocculation; heat treatment and irradiation. (Polyelectrolyte flocculation followed by centrifugation, primary drying, extruding and secondary (fluidised bed) drying constitutes a particularly valuable method of obtaining immobilised cells in a useful form). Any of these methods which do not in any particular instance destroy the activity of the inverting enzyme system may be used. It is also desirable that the chosen method should not result in leakage of the enzyme from out of the microbial cells where these have been retained intact.

Reference is made above to "an enzyme system" to cover the enzyme or enzymes needed for the reaction or reactions which achieve inversion and the possibility of any other substances present in the intact micro-organism eg. cofactors or coenzymes such as NADH or metal ions being required for efficient operation of the enzyme.

Reference is made herein to "enzymic equivalents" of the α-aryloxypropionic acids to encompass those derivatives where for example the carboxylic group is modified, eg. to salt form, which are equally well recognised by the microbial enzyme system.

It will be appreciated that the compound of formula (I) above can be an intermediate in the production of the active herbicides and hence while it is not itself a herbicide it has a herbicidal function. Thus, changes in the compound of formula I which do not affect its ability to give rise to active herbicides are also encompassed among the preferred α-aryloxypropionic acids.

The present process may also operate in respect of esters eg. the C$_1$–C$_6$, preferably C$_1$–C$_4$ alkyl esters of the compounds of formula I provided hydrolysis to the acid eg. in the presence of other microbial enzymes, can be prevented. Particularly preferred esters are the methyl, ethyl, n-propyl, isopropyl, n-butyl and ethoxyethyl esters of the acids of formula I.

The inversion reaction occurring in the process of this invention has been deduced from observations made in soil from many parts of the world. Many different soil micro-organisms may therefore potentially possess the ability to carry out the inversion. Particularly preferred for this process are bacteria, especially the Actinomycetales and related organisms, though it is also possible to use fungi.

Microorganisms which are known to have the necessary properties for performing the inversion and which have been deposited at the National Collection of Industrial and Marine Bacteria (NCIMB) Aberdeen, Scotland are:

Arthrobacter simplex (NCIB 8929); *Bacillus thuringensis* (NCIB 11992 deposited on June 25, 1984); *Leuconostoc dextranicum* (NCIB 2706); *Lactobacillus plantarum* (NCIB 6105); *Proteus vulgaris* (NCIB 67); Streptomyces sp. (NCIB 10105); and *Streptomyces venezuelae* (ATCC 15439).

In addition, a fungus Penicillium sp., deposited at the Commonwealth Mycological Institute Culture Collection (CMICC) Kew, Surrey, England as IMI 287163 and accessed on June 26, 1984, is also active.

The fungus IMI 287163 per se forms a further subject of the present invention. It may be provided in specific forms such as freeze dried, in composition with a solid or liquid diluent or as a culture in a culture medium eg. containing a source of assimilable carbon, a source of nitrogen and, if desired, vitamins and inorganic salts and/or substantially free from other micro-organisms.

The exact method of contacting the [S] enantiomer (usually in a mixture with the R enantiomer) with the microorganism or extracted enzyme system may be chosen for convenience. Clearly the contact must be of sufficient duration for the transformation (inversion) to occur. Preferably, where the contact is with immobilised whole cells, these are packed into a column and the [S] enantiomer passed through the column either in a batchwise or preferably, a continuous or semi-continuous process with the inverted [R] enantiomer being recovered at the bottom of the column. The column dimensions, rate of flow, substrate concentration, solvent and conditions of temperature and pH can be selected to give optimum yield of the [R] enantiomer. If live cells are used, the [S] enantiomer may also be separated in a column process or alternatively may be added to the culture and the product separated batchwise from the culture after a suitable period. Generally, the temperature employed will be in the range 20° to 45° C., preferably 28° to 37° C., especially about 32° C., while the pH will generally be 5 to 9, preferably 6 to 7.5, especially 6.8 to 7.2.

The [R] enantiomers of formula I are capable of giving rise to active herbicides, in particular the acids of formulae II to IX below or their salts or esters which are useful in post-emergence control of graminaceous weeds in broad-leafed crops:

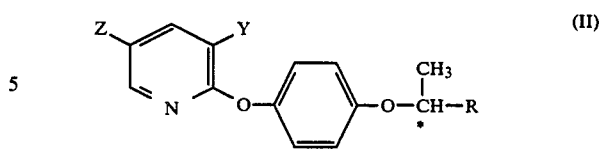

wherein Z and Y each represent fluorine, chlorine, bromine, iodine or hydrogen or a trifluoromethyl, difluoromethyl or chlorodifluoromethyl group provided that at least one of Z and Y is a halogenomethyl group or both Z and Y represent chlorine, and R represents a carboxyl group,

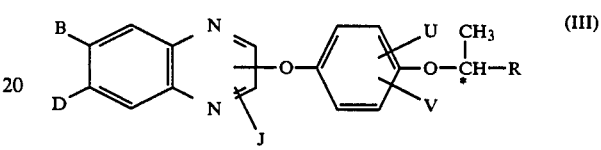

and

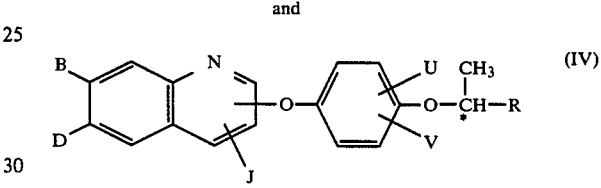

wherein B, D, J, U and V each represent hydrogen or halogen and R is as defined above;

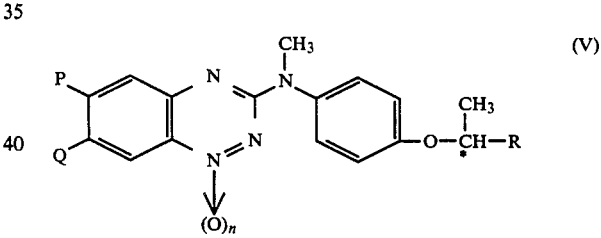

wherein one of P and Q represents halogen or trifluoromethyl and the other represents hydrogen, n is 0 or 1 and R represents a carboxyl group;

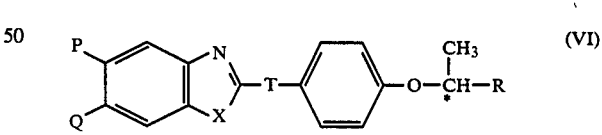

wherein X represents —O— or —S—, P, Q and R are as defined above and T represents —O— or

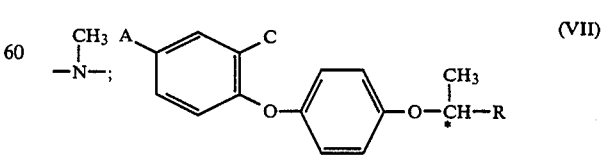

wherein A represents halogen or trifluoromethyl, C represents hydrogen, halogen or nitro and R is as defined above;

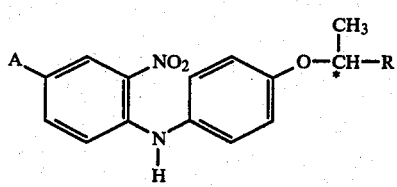

wherein A and R are as defined above;

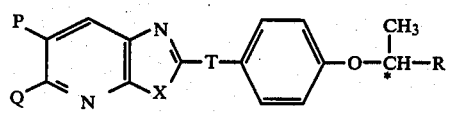

wherein P, Q, X, T and R are as defined above.

The asterisk indicates the chiral centre of these compounds.

In the compounds of formula II, preferably Z is trifluoromethyl and Y is hydrogen, chlorine or fluorine.

In the compounds of formula III and IV, preferably one of B and D is halogen eg. chlorine or fluorine and the other hydrogen, J is hydrogen and either U and V are both hydrogen or one is halogen eg. chlorine or fluorine, preferably in the 2-position, and the other is hydrogen. Desirably, when the quinoxaline or quinoline moiety is linked to the oxygen at the 2-position, B is hydrogen and D (6-position) is halogen, while when it is linked at the 3-position, D is hydrogen and B (7-position) is halogen.

In the compounds of formula V one of P and Q is preferably halogen eg. chlorine, particularly Q (7-position) and n is preferably 1.

In the compounds of formula VI, one of P and Q is preferably halogen eg. chlorine, particularly Q (6-position) when T is —O— and P (5-position) when T is

In the compounds of formula VII, A and C are preferably both halogen eg. chlorine or A is halogen eg. bromine and C is nitro or A is trifluoromethyl and C is hydrogen or halogen eg. chlorine.

In the compounds of formula VIII, A is preferably trifluoromethyl.

In the compounds of formula IX, one of P and Q is preferably halogen eg. chlorine, particularly Q (5-position) when T is —O— and P (6-position) when T is

In order to prepare these herbicides, the inverted product of formula I above will be further reacted with an appropriate compound to produce the desired herbicide as well as perhaps further processed eg. optionally salified or esterified. Where the desired herbicide is of formula II to IX, the appropriate compound for the reaction will be of formula:

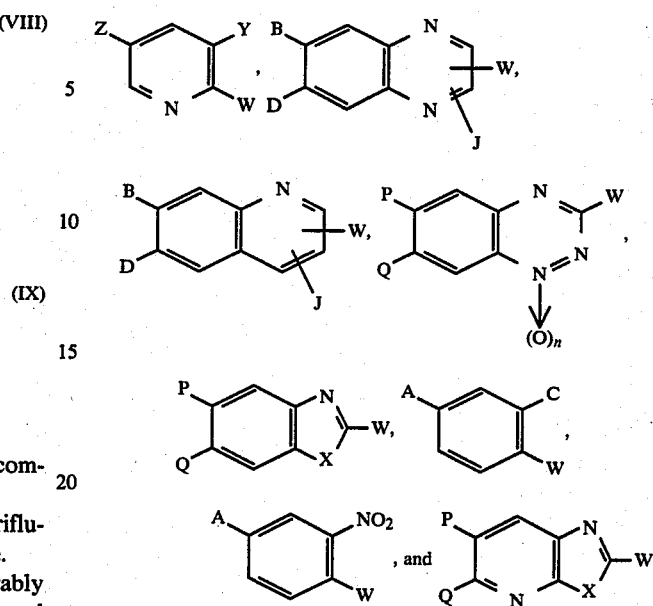

respectively, wherein Z, Y, B, D, J, P, Q, n, X, A and C are as defined above and W is a leaving group eg. halogen, preferably chlorine.

When the compounds of formulae II to IX are in free acid form they are then preferably esterified to produce the preferred esters as follows: the methyl, n-propyl n-butyl, or ethoxyethyl ester of the acids of formula II when one of Z and Y is a halogenomethyl group eg. the n-butyl ester of 2[4(5-trifluoromethylpyridyl-2-oxy)-phenoxy]propionic acid and the methyl, propyl or ethoxyethyl ester of 2[4(3-chloro-5-trifluoromethyl-pyridyl-2-oxy)phenoxy]propionic acid; the propargyl ester of the acids of formula II when Z and Y are both chlorine; the ethyl or n-propyl ester of the acids of formulae III and IV; the isopropyl ester of the acid of formula V; the methyl and ethyl esters of the acids of formulae VI, VII and VIII and the methyl, ethyl and butyl esters of the acids of formula IX. Also preferred herbicidal products are compounds of formula II to IX with slight changes in substitution, particularly in the rings, where these substituents do not alter substantially the enzyme recognition nor the herbicidal activity or function of the compound.

These further processing steps to produce indirect products of the inversion process also form a subject of the present invention.

The indirect products of the present inversion process are capable of inhibiting the growth of unwanted graminaceous plants when applied in a herbicidally effective amount and, in particular, can inhibit the growth of graminaceous weeds among dicotyledonous crop plants if applied to the area of a crop in an amount sufficient to inhibit the growth of the weeds but insufficient to damage the crop substantially.

The rate at which the compounds are usually applied in inhibiting the growth of weeds will depend upon factors such as the identity of the particular graminaceous weeds and broad-leafed crop, but in general 0.025 to 2.5 kg per hectare is suitable, with 0.1 to 1 kg per hectare being preferred.

The indirect products are usually applied as herbicidal compositions, comprising the indirect products as active ingredient together with a suitable solid or liquid diluent and optionally a further herbicidal compound or compounds, either having a similar spectrum of activity or a complementary activity to that of the first active compound.

The invention is illustrated by the following Examples.

EXAMPLE 1

A 50 μg/ml solution (A) of RS 2-(para-hydroxyphenoxy)propionic acid in dextrose-peptone broth was prepared and a plate culture of Arthrobacter simplex (NCIB 8929) was grown for 2 days in dextrose-peptone broth at 28° C. without shaking. 2 ml of the solution (A) was transferred to a sterile test tube and innoculated with the microorganism culture via a sterile loop which was then further incubated at 28° C. for 7 days.

After the 7 day reaction, 1 ml of the solution was removed and the product stereoselectivity analysed by high performance liquid chromatography (HPLC) using a method based on that of Y. Tapuhi et al in J. Chromatography 205 325–337. The percentage [R] isomer in the product was found to be 57%.

EXAMPLE 2

The procedure of Example 1 was repeated but using the following microorganisms incubated at the specified temperature to give the indicated percentage [R] enantiomer in the products.

| Microorganism | Temperature | % [R] enantiomer |
|---|---|---|
| Bacillus thuringensis (NCIB 11992) | 28° C. | 77% |
| *Leuconostoc dextranicum (NCIB 2706) | 37° C. | 75% |
| *Lactobacillus plantarum (NCIB 6105) | 37° C. | 58% |
| Proteus vulgaris (NCIB 67) | 37° C. | 57% |
| Streptomyces sp. (NCIB 10105) | 28° C. | 64% |
| Streptomyces venezuelae (ATCC 15439) | 28° C. | 57% |
| Penicillium sp. (IMI 287163) | 28° C. | 68% |

*Instead of dextrose-peptone broth, MRS medium (OXOID code No. CMI 361) was used.

I claim:

1. A process for the stereospecific inversion of the [S] enantiomer of an α-aryloxypropionic acid of formula I:

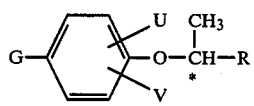
(I)

wherein G is OR¹ or

R¹ is hydrogen or a protecting group and R² is hydrogen or methyl, U and V each independently represent hydrogen or halogen, and R is a carboxyl group, or an enzymic equivalent thereof, in a mixture of the [R] and [S] enantiomers which process comprises contacting said [S] enantiomer in said mixture with a stereospecific inverting enzyme so as to convert the [S] enantiomer to the corresponding [R] enantiomer without substantially affecting the [R] enantiomer.

2. A process according to claim 1 wherein the enzyme comprises a bacterium.

3. A process according to claim 2 wherein the bacterium is chosen from the Actinomycetales organisms.

4. A process according to claim 1 wherein the enzyme comprises:

Arthrobacter simplex (NCIB 8929), *Bacillus thuringensis* (NCIB 11992), *Leuconostoc dextranicum* (NCIB 2706), *Lactobacillus plantarum* (NCIB 6105), *Proteus vulgaris* (NCIB 67), Streptomyces sp. (NCIB 10105), *Streptomyces venezuelae* (ATCC 15439) or Penicillium sp. (IMI 287163).

5. A process according to claim 1 wherein G in formula I is OR¹.

6. A process according to claim 1 wherein the enzyme is immobilised and contained in a column through which the [S] enantiomer is passed.

7. A process according to claim 1 wherein the product of the stereospecific inversion is subsequently reacted with a compound of formula:

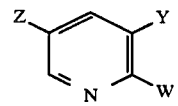

wherein Z and Y each represent fluorine, chlorine, bromine, iodine or hydrogen or a trifluoromethyl, difluoromethyl or chlorodifluoromethyl group and W is a leaving group to produce a compound of formula II:

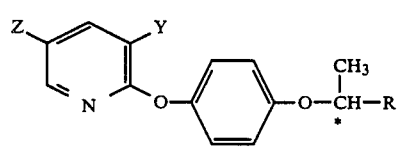
(II)

wherein Z and Y are as defined above and R is provided by the compound of formula I.

8. A process according to claim 7 wherein the product of formula II is 2[4(5-trifluoromethylpyridyl-2-oxy)phenoxy]propionic acid or 2[4(3-chloro-5-trifluoromethylpyridyl-2-oxy)phenoxy]propionic acid or an ester thereof.

9. A process according to claim 1 wherein the product of the stereospecific inversion is subsequently reacted with a compound of formula:

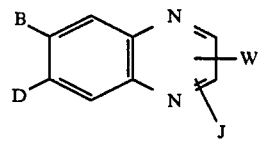

wherein B, D and J each represent hydrogen or halogen and W is a leaving group to produce a compound of formula:

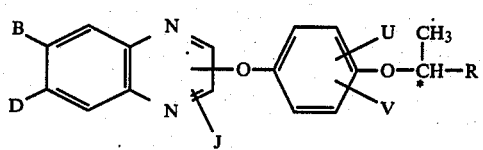
(III)
wherein B, D, J, U and V each represent hydrogen or halogen and R is provided by the compound of formula I.
10. A process according to claim 9 wherein one of B and D is chloro and the other hydrogen, U is hydrogen or 2-fluoro and J and V each represent hydrogen.
11. A process according to claim 1 wherein the product in the form of a free acid and this is subsequently esterified.
* * * * *